(12) United States Patent
Tanabe

(10) Patent No.: US 9,187,781 B2
(45) Date of Patent: Nov. 17, 2015

(54) POLYMORPHISM IDENTIFICATION METHOD

(75) Inventor: Tetsuya Tanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 623 days.

(21) Appl. No.: 12/759,118

(22) Filed: Apr. 13, 2010

(65) Prior Publication Data

US 2010/0267036 A1    Oct. 21, 2010

(30) Foreign Application Priority Data

Apr. 20, 2009  (JP) .............................. P2009-101670

(51) Int. Cl.
*C12Q 1/68*   (2006.01)

(52) U.S. Cl.
CPC ................ *C12Q 1/6827* (2013.01); *C12Q 1/68* (2013.01)

(58) Field of Classification Search
CPC ....................................................... C12Q 1/68
USPC .......................................................... 435/6.1
See application file for complete search history.

(56) References Cited

U.S. PATENT DOCUMENTS 6,326,145 B1 * 12/2001 Whitcombe et al. ............... 435/5

FOREIGN PATENT DOCUMENTS

| JP | 2003-534764 A | 11/2003 |
|----|---------------|---------|
| JP | 2005-511096 A | 4/2005 |
| JP | 2008-516584 A | 5/2008 |
| WO | 99-66071 A1 | 12/1999 |
| WO | 03/050305 A1 | 6/2003 |
| WO | WO 2005/012571 A1 | 2/2005 |
| WO | 2006/005074 A2 | 1/2006 |

OTHER PUBLICATIONS

Solinas et al. (Nucleic Acids Res. Oct. 15, 2001;29(20):E96).*
Fortina et al. (Mol Cell Probes. Aug. 1992;6(4):353-6).*
Thelwell et al. Mode of action and application of Scorpion primers to mutation detection. Nucleic Acids Research 2000;28(19):3752-61.*
Japanese Office Action dated Oct. 29, 2013 issued in JP 2009-101670 together with English translation.

* cited by examiner

*Primary Examiner* — Ardin Marschel
(74) *Attorney, Agent, or Firm* — Scully, Scott, Murphy & Presser, P.C.

(57) ABSTRACT

The present invention is to provide a method for identifying a polymorphism. The method includes performing a nucleic acid chain extension reaction and identifying the polymorphism of the nucleic acid contained in the test nucleic acid sample. The extension reaction is conducted with use of a nucleic acid in a test nucleic acid sample as a template, a type I detection primer which hybridizes with a region including the polymorphic site of a nucleic acid whose polymorphic site nucleotide sequence consisting of a first nucleotide sequence, and a polymerase. The reaction is conducted with the presence of an inhibitory oligonucleotide, which hybridizes with the type I detection primer. The region of the type I detection primer to hybridize with the inhibitory oligonucleotide is located on the 5' side of the polymorphism detection site of the type I detection primer to hybridize with the polymorphic site.

12 Claims, 3 Drawing Sheets

Wt: atcgaggatttccttgttggctttcggagatgttgcttctcttaattccttgatagcgacgggaattttaactttctcaccttc
Mt: atcgaggatttccttgttggctttcggagatgtt----------------ttgatagcgacgggaattttaactttctcaccttc

FIG. 5

Wt 1st PCR product
AGGGAAAGACATAGAAAGTGAAcatttaggatgtggagatgagcagggtctagagcagagcagctgccagacatgagaaa
aggtgggcctgaggttcagagccatggaccccacacagcaaagcagaaactcacatcgaggatttccttgttggcttt
cggagatgttgcttctcttaattccttgatagcgacgggaattttaactttctcaccttctgggatccagagtccctat
gacagagagagaaggaagacgttaactggcaattgtgagatggtgccacatgctgcccagtgatctgggtggatgttacc
agcgatgcaccccgaaggtgagggacactggggctgtggagccgcacctaaggctgatattgctgggggctgtgacgccc
ccgcagccctgcagctgttgggcTCCACGAATCACACTGATTA Mt 1st PCR product
AGGGAAAGACATAGAAAGTGAAcatttaggatgtggagatgagcagggtctagagcagagcagctgccagacatgagaaa aggtgggcctgaggttcagagccatggaccccacacagcaaagcagaaactcacatcgaggatttccttgttggcttt cggagatgttttgatagcgacgggaattttaactttctcaccttctgggatccagagtccctatgacagagagagaagg
aagacgttaactggcaattgtgagatggtgccacatgctgcccagtgatctgggtggatgttaccagcgatgcaccccga
aggtgagggacactggggctgtggagccgcacctaaggctgatattgctgggggctgtgacgccccgcagccctgcagc
tgttgggcTCCACGAATCACACTGATTA

FIG. 6

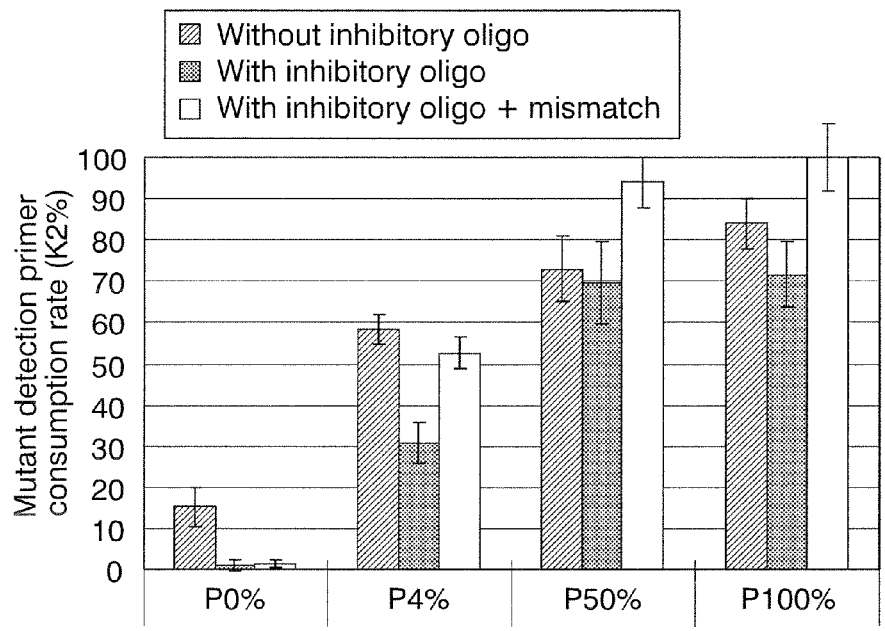

POLYMORPHISM IDENTIFICATION METHOD

BACKGROUND OF THE INVENTION

1. Field of the Invention

The present invention relates to a method for identifying a polymorphism more sensitively and more accurately than prior art methods.

2. Description of Related Art

With the recent progress in genetic engineering technologies and gene recombination technologies, genetic tests through nucleic acid analyses have been widely used in applications to medical services, researches, and industries. Such tests are to detect the presence of DNA which has a target nucleotide sequence within a sample, and have been applied not only to diagnosis and treatment of diseases, but also to food inspection and other various fields. In particular, a genetic polymorphism such as a SNP (Single Nucleotide Polymorphism) is considered to be a major factor contributing to the individual difference in the vulnerability against a specific disease such as cancer, the drug metabolizing capacity, and so forth. Genetic polymorphism analyses have been widely conducted not only in academic researches but also in actual clinical tests. Therefore, highly accurate and quick methods for detecting a genetic polymorphism have been enthusiastically developed.

As to the method for detecting and identifying a genetic polymorphism, there are many reported methods in which artificially synthesized polynucleotides such as probes and primers are used to examine the nucleotide sequences of nucleic acids. For example, some methods are to analyze the nucleotide sequence of a SNP serving as the analysis target and its neighboring region by molecular-biological enzymatic reactions. Such methods can be exemplified by: a method in which a region including a polymorphism such as a SNP can be detected by PCR (Polymerase Chain Reaction) amplification; and a method in which a SNP can be detected by a ligation reaction using a probe including the detection target SNP at the 3' end and a probe including a nucleotide adjacent to the 5' side of the SNP, at the 5' end, and subsequent determination regarding the obtainability of a polynucleotide bound with these two probes.

In particular, often employed SNP analysis methods are SSP-PCR (Sequence Specific Primer-PCR) method and ASP-PCR (Allele Specific Primer-PCR) method, in which a SNP can be detected by PCR using a primer specifically bindable to a specific nucleotide sequence, allele, and the like, and subsequent determination regarding the presence/absence of the PCR product. The reason is that, since the detection and recognition of a nucleotide sequence (genetic polymorphism) can be carried out concurrently with enhancement of its signal, the polymorphism detection by means of the SSP/ASP-PCR method can enable the SNP detection even in the case where only a small amount of specimen is available, or the case where the nucleic acid concentration in a sample is very low, like a case of a specimen in a clinical test, and therefore these methods are very useful.

There are many reported SNP analysis methods using no amplification reaction, unlike the SSP-PCR method and the ASP-PCR method. For example, there is disclosed a method (1) for detecting a SNP by using (a) a partially-double-stranded nucleic acid molecule comprising: a single-stranded nucleic acid molecule complementary to a nucleic acid molecule as a detection target; and (b) one or two single-stranded nucleic acid molecule(s) hybridizing with a part of the single-stranded nucleic acid molecule (a), wherein regions of single-stranded structure of the partially-double-stranded nucleic acid molecule are complementary to regions including the identification site of the nucleic acid molecule as the detection target (for example, refer to Patent Document 1). Under the coexistence of the partially-double-stranded nucleic acid molecule and the nucleic acid molecule as the detection target, the single-strand of the nucleic acid molecule of the invention and the target nucleic acid molecule are replaced by the strand displacement reaction, thereby forming a double-stranded structure of the long chain of the nucleic acid molecule of the invention and the target nucleic acid molecule. The target nucleic acid molecule can be detected by detecting this double-stranded structure.

REFERENCE

Patent Document

Patent Document 1: PCT International Publication No. WO05/012571 pamphlet

SUMMARY OF THE INVENTION

The SSP-PCR method and the ASP-PCR method involve a problem in that, due to a low flexibility in the design of the primer nucleotide sequence, sufficient sensitivity may not be achieved depending on the nucleotide sequence of the target genetic polymorphism to identify.

On the other hand, the above-mentioned method (1) is a detection method using hybridization, not using a chain extension reaction, and therefore is not capable of signal amplification. For this reason, it is difficult to detect a genetic polymorphism with sufficient sensitivity from a sample like a clinical specimen which contains a very small amount of nucleic acid from the beginning. In addition, since the strand displacement reaction is used, depending on the nucleotide sequence of the genetic polymorphism as the identification target, upon the identification of the genetic polymorphism, it can easily hybridize with a nucleic acid molecule having a different type of nucleotide sequence from that of the detection target of the partially-double-stranded nucleic acid molecule, with relatively high stability. Therefore, it is highly possible to cause the strand displacement reaction, leading to insufficient identification accuracy.

It is an object of the present invention to provide a method for identifying a polymorphism more sensitively and more accurately with use of the SSP-PCR method or the ASP-PCR method.

In view of the above-mentioned problems, the inventors of the present invention have conducted intensive studies. As a result, they have discovered that a nonspecific-nucleic acid extension reaction can be inhibited and thereby the polymorphism identification accuracy can be improved in the SSP-PCR method or the ASP-PCR method, by adding an oligonucleotide into a reaction solution when performing a nucleic acid extension reaction to cause hybridization between a template nucleic acid and a primer which can specifically hybridize with a certain type of polymorphic allele, wherein the oligonucleotide can hybridize with a region of the primer located on the 5' side of the polymorphism detection site of the primer. This has led to the completion of the present invention.

That is, the present invention provides:

(1) a polymorphism identification method for identifying a polymorphism of a polymorphic site-containing nucleic acid, comprising:

(a) performing a nucleic acid chain extension reaction with use of a nucleic acid in a test nucleic acid sample as a template, a type I detection primer, and a polymerase, with the presence of an inhibitory oligonucleotide, the type I detection primer being a primer which can hybridize with the nucleic acid in a region including the polymorphic site thereof whose polymorphic site nucleotide sequence consisting of a first nucleotide sequence, and the inhibitory oligonucleotide being an oligonucleotide which can hybridize with the type I detection primer; and (b) identifying the polymorphism of the nucleic acid contained in the test nucleic acid sample, based on whether or not the type I detection primer has been extended in step (a), wherein the region of the type I detection primer which hybridizes with the inhibitory oligonucleotide is located on the 5' side of a polymorphism detection site of the type I detection primer which hybridizes with the polymorphic site;

(2) the polymorphism identification method according to (1), wherein the nucleotide sequence of the region of said inhibitory oligonucleotide to hybridize with the type I detection primer includes at least one nucleotide mismatch, with respect to the nucleotide sequence of the region of the type I detection primer which hybridizes with the inhibitory oligonucleotide;

(3) the polymorphism identification method according to either one of (1) and (2), wherein the 3'-end nucleotide of the inhibitory oligonucleotide is blocked so that the oligonucleotide has no function as a primer;

(4) the polymorphism identification method according to any one of (1) through (3), wherein the length of the region on the 3' side from the region of the type I detection primer to hybridize with the inhibitory oligonucleotide is five nucleotides or more;

(5) the polymorphism identification method according to any one of (1) through (4), wherein the length of the region of the type I detection primer to hybridize with the inhibitory oligonucleotide is ten nucleotides or more;

(6) the polymorphism identification method according to any one of (1) through (4), wherein the nucleic acid chain extension reaction comprises:

(i) denaturing the nucleic acid in the test nucleic acid sample into single strands;

(ii) annealing the single-stranded nucleic acid with the type I detection primer or the inhibitory oligonucleotide; and (iii) extending the nucleic acid strand starting from the type I detection primer, wherein a Tm value of a hybrid between the type I detection primer and the inhibitory oligonucleotide is higher than the temperature of (ii), and lower than the temperature of step (a);

(7) the polymorphism identification method according to any one of (1) through (5), wherein the polymorphism detection site of the type I detection primer which hybridizes with the polymorphic site is located at its 3' end;

(8) the polymorphism identification method according to either one of (6) and (7), wherein a cycle consisting of (i), (ii), and (iii) is repeated twice or more times in the nucleic acid chain extension reaction;

(9) the polymorphism identification method according to any one of (1) through (8), wherein the nucleic acid chain extension reaction is performed on a nucleic acid whose polymorphic site nucleotide sequence is different from the first nucleotide sequence with the presence of a detection primer which can hybridize with a region including the polymorphic site thereof;

(10) a polymorphism identification kit for use in the identification of a polymorphism of a polymorphic site-containing nucleic acid, comprising:

a type I detection primer which can hybridize with a nucleic acid in a region including the polymorphic site thereof whose nucleotide sequence consisting of a first nucleotide sequence;

an inhibitory oligonucleotide which can hybridize with the type I detection primer, wherein the region of the type I detection primer which hybridizes with the inhibitory oligonucleotide is located on the 5' side of the polymorphism detection site of the type I detection primer to hybridize with the polymorphic site.

With use of the polymorphism identification method of the present invention, a nonspecific-nucleic acid extension reaction can be efficiently inhibited and thereby the polymorphism can be accurately and sensitively identified in the SSP-PCR method or the ASP-PCR method where the flexibility in the design of the polymorphism detection primer has been low so far. Particularly, it is possible to sensitively detect or identify a polymorphism such as a somatic mutation which has been so far difficult to detect or identify by conventional SSP-PCR or like method.

BRIEF DESCRIPTION OF THE DRAWINGS

FIG. 5 shows the nucleotide sequences of the first PCR products (SEQ. ID. NO. 10 and SEQ. ID. NO. 11) of the example 1.

FIG. 6 is a graph showing the consumption rate (K2%) of the mutant detection primer with variations of the content ratio of the mutant nucleic acid, measured in the example 1.

DETAILED DESCRIPTION OF THE INVENTION

Figure 1:
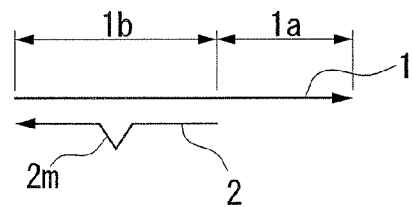
FIG. 1 is a schematic diagram showing a hybrid between a type I detection primer (1) and an inhibitory oligonucleotide (2).

The term "polymorphism" used in the present invention refers to an occurrence of variation in the nucleotide sequence of a same gene, between individuals within a certain group of biological species, or between cells within a same individual. Specifically, a specific nucleotide sequence of a gene derived from a certain cell may be different from a corresponding nucleotide sequence of the same gene derived from another individual of the same biological species, or another cell of the same individual, due to substitution, deletion, or insertion of one or a plurality of nucleotide(s); in which case, the gene is regarded to be polymorphic, and the site whose nucleotide sequence varies between both parties is referred to as the polymorphic site. The polymorphism may occur either in genomic DNA or in mitochondrial DNA.

The term "polymorphic site" used in the present invention refers to a site of a gene whose nucleotide sequence varies per each polymorphism. For example, assuming that in a genetic polymorphism caused by substitution, a first type (type I) nucleotide sequence is gggaaa and another non-type I (type II) nucleotide sequence is ggcaaa; the third nucleotide from the 5' side, g in the type I and c in the type II, is regarded as the polymorphic site. On the other hand, assuming that in a genetic polymorphism caused by deletion or insertion, a first type (type I) nucleotide sequence is gggcccaaa and another non-type I (type II) nucleotide sequence is gggaaa; the fourth to sixth nucleotides from the 5' side (ccc) of the type I is regarded as the polymorphic site and similarly the missing part between the third and the fourth nucleotides from the 5' side of the type II is regarded as the polymorphic site.

In addition, the term "to identify a polymorphism" used in the present invention means to identify whether or not the polymorphic site nucleotide sequence of a nucleic acid contained in a test nucleic acid sample is the same as that of a certain kind of polymorphism. Accordingly, the nucleotide sequence of the polymorphism serving as the target of the polymorphism identification method of the present invention has to be elucidated to an extent which allows such identification.

The polymorphism serving as the identification target in the present invention is not specifically limited as long as the polymorphism satisfies the abovementioned provisions and its nucleotide sequence has been elucidated to a detectable degree by a gene recombination or like technique. In addition, the polymorphism may be either inherent or acquired as often seen in tumor cells or like. Examples of such a polymorphism includes a single nucleotide polymorphism (SNP), a microsatellite, and a somatic mutation.

The test nucleic acid sample in the present invention is not specifically limited as long as the sample contains a nucleic acid which has a polymorphism to identify. The test nucleic acid sample may be a biological sample collected from an animal or the like, a sample prepared from a cultured cell lysate or the like, and a nucleic acid solution extracted and purified from a biological sample or the like. In particular, human-derived biological samples to be used for clinical or other tests and nucleic acid samples extracted and purified from such human-derived biological samples are preferred. Examples of such human-derived biological samples can include blood, bone marrow, lymph fluid, urea, sputum, ascites fluid, exudate fluid, amniotic fluid, peritoneal lavage fluid, lung lavage fluid, bronchial lavage fluid, bladder lavage fluid, pancreatic juice, saliva, semen, bile, and feces. In addition, the test nucleic acid sample may be directly used after the collection from an organism, or may be prepared before use. The preparation method is not specifically limited as long as DNA, RNA, or such a nucleic acid contained in the biological sample is not impaired, and a usual preparation method for biological samples can be applied. Besides, DNA extracted and purified from a biological sample and amplified by a PCR or like method, and cDNA synthesized from RNA contained in a biological sample with a reverse transcriptase may also be used. When DNA or the like extracted and purified from a biological sample is used, it is possible to amplify the polymorphic site-containing nucleic acid contained therein by PCR and to use the thus yielded amplification product as the test nucleic acid sample.

The polymorphism identification method of the present invention is a method to identify a polymorphism of a polymorphic site-containing nucleic acid, comprising performing a nucleic acid chain extension reaction with use of a type I detection primer which can specifically hybridize with a type (type I) of a polymorphism, with the presence of an oligonucleotide which can hybridize with a region of the type I detection primer located on the 5' side of the polymorphism detection site. The term "polymorphism detection site" means a partial region of the detection primer which can hybridize with the polymorphic site of a nucleic acid.

The term "type I detection primer" used in the present invention refers to a primer which can hybridize with a region including the polymorphic site of a nucleic acid whose polymorphic site of the identification target polymorphism consists of a first nucleotide sequence (hereinunder, may be referred to as the "type I nucleic acid"). The type I detection primer may be any kind of primer which can hybridize with a partial region of the type I nucleic acid which contains the polymorphic site. The type I detection primer may be an oligonucleotide which comprises a nucleotide sequence completely complementary to the nucleotide sequence of the type I nucleic acid, or an oligonucleotide which comprises a nucleotide sequence complementary thereto except for one or several nucleotide mismatch(es). Preferably, the type I detection primer of the present invention is an oligonucleotide which comprises a nucleotide sequence completely complementary to the nucleotide sequence of the type I nucleic acid, as it can offer higher identification accuracy.

In addition, the type I detection primer may also have on its 5' side an additional nucleotide sequence besides the region which can hybridize with the type I nucleic acid. Examples of such an additional sequence include a restriction enzyme recognition sequence and a sequence for labeling the nucleic acid.

Furthermore, the type I detection primer may be labeled so as to facilitate the detection of the extension product starting from the primer. The labeling substance is not specifically limited as long as it can be used for labeling nucleic acids. Examples thereof can include radioisotopes, fluorophores, chemiluminescent substances, and biotin.

It is preferable to design the type I detection primer so that its polymorphism detection site which can hybridize with the polymorphic site of the first nucleic acid can be located at the 3' side, rather than the 5' side, of the primer. In particular, it is more preferable to design the type I detection primer so that its polymorphism detection site can be located within five nucleotides from the 3' end of the primer, more preferably within two nucleotides from the 3' end thereof, and particularly preferably at the 3' end.

The term "inhibitory oligonucleotide" used in the present invention refers to an oligonucleotide which can hybridize with the type I detection primer, wherein the region of the type I detection primer to hybridize with the inhibitory oligonucleotide is located on the 5' side of the polymorphism detection site of the type I detection primer to hybridize with the polymorphic site.

That is, the type I detection primer has a polymorphism detection site on its 3' side, and a region on the 5' side from the polymorphism detection site of the type I detection primer can hybridize with the inhibitory oligonucleotide. Hereinunder, the region of the type I detection primer to hybridize with the inhibitory oligonucleotide is referred to as a "common region", and the region on the 3' side from this common region is referred to as a "polymorphism detection region". The polymorphism detection site of the type I detection primer is located in this polymorphism detection region. FIG. 1 is a schematic diagram showing a hybrid between the type I detection primer (1) and the inhibitory oligonucleotide (2). In this figure, the region 1a represents the polymorphism detection region and the region 1b represents the common region.

The type I detection primer can hybridize not only with the type I nucleic acid but also with a nucleic acid whose polymorphic site consists of a second nucleotide sequence (hereinunder, may be referred to as the "type II nucleic acid"), under a low-temperature environment including the annealing step of the nucleic acid chain extension reaction. In this manner, the type I detection primer does hybridize with the type II nucleic acid, and the nonspecific-nucleic acid chain extension reaction does occur. This leads to a worsening of the polymorphism identification accuracy.

The second nucleotide sequence refers to another nucleotide sequence of the polymorphic site regarding the identification target polymorphism, which is different from the first nucleotide sequence. For example, if the identification target polymorphism is a SNP having two types of polymorphism, namely a wild-type and a mutant, the nucleotide sequence of the mutant can be regarded as the first nucleotide sequence and the nucleotide sequence of the wild-type can be regarded as the second nucleotide sequence. In addition, if the identification target polymorphism is a somatic mutation, the nucleotide sequence of the mutant can be regarded as the first nucleotide sequence and the nucleotide sequence of the normal type can be regarded as the second nucleotide sequence. If the polymorphism has three types of polymorphic site nucleotide sequences, either type of the nucleotide sequences other than the first nucleotide sequence can be selected as the second nucleotide sequence.

Figure 2:
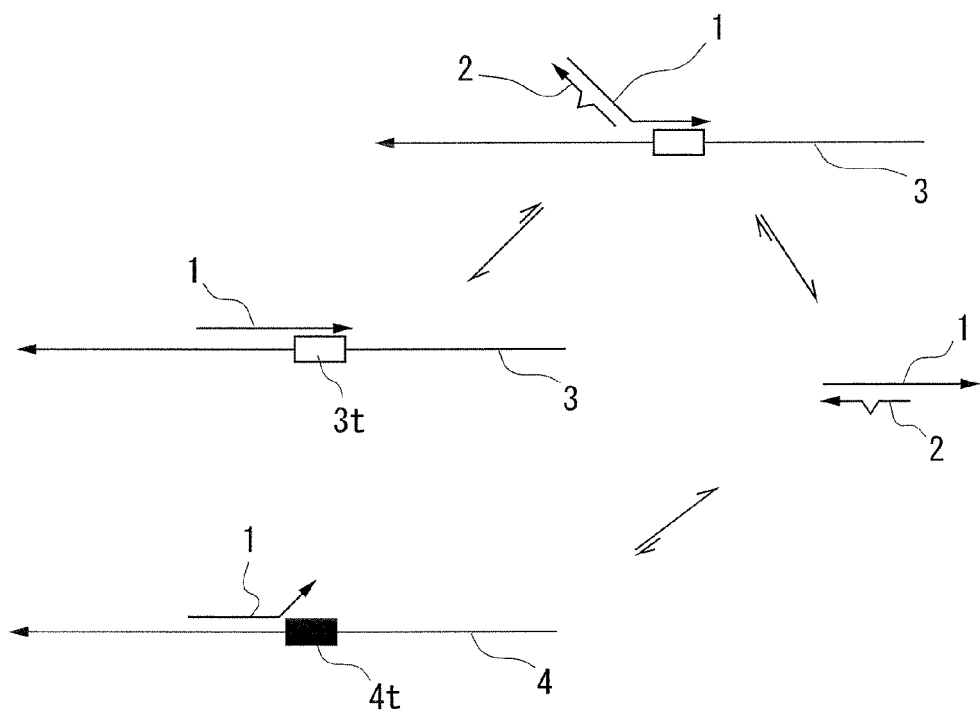
FIG. 2 is a schematic diagram showing hybrids formed in a solution containing a type I nucleic acid, a type II nucleic acid, the type I detection primer, and the inhibitory oligonucleotide.

FIG. 2 is a schematic diagram showing hybrids formed in a solution containing the type I nucleic acid, the type II nucleic acid, the type I detection primer, and the inhibitory oligonucleotide. The type I detection primer (1) can hybridize not only with the type I nucleic acid (3) but also with the type II nucleic acid (4) in the region other than the polymorphic site. On the other hand, the solution also contains a hybrid between the type I detection primer (1) and the inhibitory oligonucleotide (2). In addition, the hybrid between the type I detection primer (1) and the inhibitory oligonucleotide (2) can be expected to be in a dynamic and equilibrium state with respect to the hybrid between the type I detection primer (1) and the type I nucleic acid (3), via the hybrid of these three parties. On the other hand, the hybrid between the type I detection primer (1) and the inhibitory oligonucleotide (2) is also in a dynamic and equilibrium state with respect to the hybrid between the type I detection primer (1) and type II nucleic acid (4).

The polymorphism identification method of the present invention creates an equilibrium state as shown in FIG. 2 by employing such an inhibitory oligonucleotide which can hybridize with the type I detection primer, so as to thereby inhibit the nucleic acid chain extension under a low-temperature environment such as the annealing step, and to destabilize the hybrid between the type I detection primer and the non-type I nucleic acid. Therefore, the nonspecific-nucleic acid chain extension reaction starting from the type I detection primer can be efficiently inhibited, as a result of which the polymorphism identification accuracy can be expected to improve.

It may be quite difficult for prior art SSP-PCR to identify a polymorphism, depending on the sequence of the neighboring region of the polymorphic site. Even in such a case, the polymorphism identification method of the present invention is able to demonstrate its effects since the identification accuracy is improved by hybridization between the inhibitory oligonucleotide and the region other than the polymorphism detection site of the type I detection primer.

The lengths of the polymorphism detection region and the common region of the type I detection primer are not specifically limited as long as these lengths can make the stability of the hybrid formed of the type I detection primer (1), the inhibitory oligonucleotide (2), and the type I nucleic acid (3) higher than that of the hybrid between the type I detection primer (1) and the inhibitory oligonucleotide (2) as shown in FIG. 2. The lengths can be appropriately determined with consideration of the nucleotide sequences of these three parties, the reaction condition of the nucleic acid chain extension reaction, and the like. Specifically, when a typical reaction condition is employed, the type I detection primer preferably has the polymorphism detection region in a length of five nucleotides or longer, and the common region in a length of ten nucleotides or longer.

Figures 3, 4:
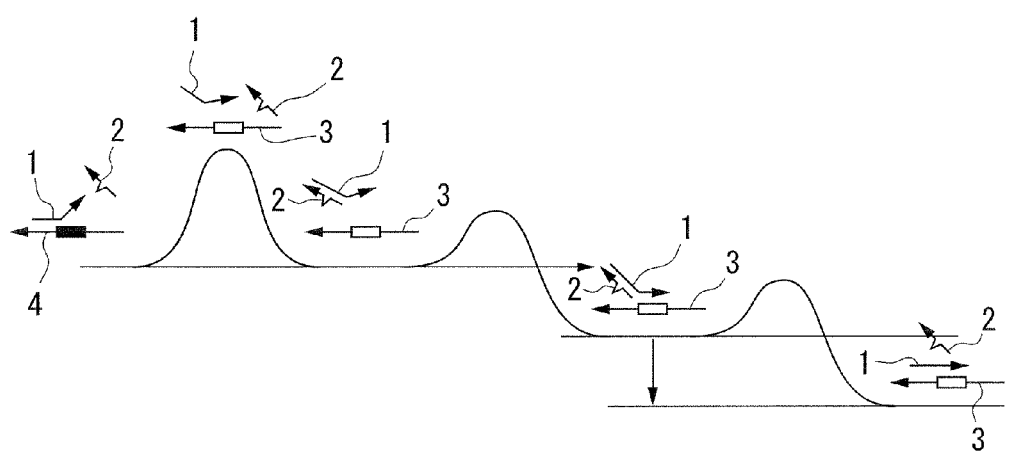
FIG. 3 is a schematic diagram showing a desirable relation of the stabilities of the various types of hybrids of FIG. 2.
FIG. 4 shows the alignments of the nucleotide sequences of the polymorphic site and its neighboring region of the wild-type (Wt: SEQ. ID. NO 7) and the mutant (Mt:SEQ. ID. NO. 8 (5' side sequence) and SEQ. ID. NO. 9 (3' side sequence)) of the EGFR gene in the example 1.

In order to promote the specific nucleic acid chain extension reaction while inhibiting the nonspecific-nucleic acid chain extension reaction, the type I detection primer and the inhibitory oligonucleotide are preferably designed so that the hybrid between the type I detection primer and the type I nucleic acid can have the highest stability among the various types of hybrids shown in FIG. 2. FIG. 3 is a schematic diagram showing a desirable relation of the stabilities of the various types of hybrids of FIG. 2. The setting is such that the stability of the hybrid between the type I detection primer and the type II nucleic acid formed by the nonspecific-reaction would be the lowest, and the stability of the hybrid between the type I detection primer and the type I nucleic acid formed by the specific reaction of interest would be the highest. Furthermore, these designs are made so that the energy level of the hybrid formed by the three parties of the type I detection primer, the inhibitory oligonucleotide, and the type I nucleic acid would be lower than the energy level of a state where the type I nucleic acid is separated from the hybrid between the two parties of the type I detection primer and the inhibitory oligonucleotide, and the energy level of the hybrid between the type I detection primer and the type I nucleic acid would be lower than the hybrid formed by the three parties.

It is preferable that at least one nucleotide mismatch is included in the nucleotide sequence of the region of the inhibitory oligonucleotide to hybridize with the type I detection primer, with respect to the nucleotide sequence of the common region of the type I detection primer (the region to hybridize with the inhibitory oligonucleotide). By including the mismatch nucleotide(s) into the inhibitory oligonucleotide, the stability of the hybrid between the type I detection primer and the type I nucleic acid can be higher than the stability of the hybrid formed by the three parties of the type I detection primer, the inhibitory oligonucleotide, and the type I nucleic acid.

The term "mismatch" used in this application means a site incapable of forming a base pair through hydrogen bonding (a site whose base(s) is(are) not complementary to the counterpart base(s)) when two oligonucleotides (or single-stranded nucleic acids) are being hybridized with each other to form a hybrid therebetween.

In addition, it is preferable that the various types of hybrids as shown in FIG. 2 are at equilibrium under the annealing condition, and that the inhibitory oligonucleotide separates from the type I detection primer at the time of the nucleic acid chain extension reaction. The reason is that, by designing the inhibitory oligonucleotide in this way, it becomes possible to exclusively inhibit the nonspecific-nucleic acid chain extension reaction without inhibiting the nucleic acid chain extension reaction of interest starting from the type I detection primer with the template type I nucleic acid.

Specifically, when the nucleic acid chain extension reaction comprises a denaturation step for denaturing the nucleic acid in the test nucleic acid sample into single strands, and an annealing step for hybridizing between the single-stranded nucleic acid and the type I detection primer or the inhibitory oligonucleotide; it is preferable to design the inhibitory oligonucleotide so that the Tm value of the hybrid between the type I detection primer and the inhibitory oligonucleotide would be higher than the temperature of the annealing step and lower than the temperature of the extension step.

In the present invention, the Tm values of the detection primer and the inhibitory oligonucleotide can be calculated based on their nucleotide sequences by a usual method.

This calculation can also be done by using a simulation software available in the market such as the Visual OMP (manufactured by DNA Software).

Moreover, preferably, the inhibitory oligonucleotide is a kind of oligonucleotide which has no function as a primer. Here, the term "no function as a primer" means no bindability of the 3'-end nucleotide of the oligonucleotide to any new nucleotide even with the aid of a polymerase, and thus means no capability to extend a nucleic acid chain. Specifically, such a kind of oligonucleotide which has no function as a primer can be made by blocking the 3'-end nucleotide. The 3'-end nucleotide can be blocked by any known method in the art. Examples of such a blocking method can include; a method for substituting the hydroxyl group at the 3' position of the 3'-end of the inhibitory oligonucleotide with a functional group other than the hydroxyl group, a method for substituting the 3'-end nucleotide with a dideoxy nucleotide, and a method for binding a dye, a fluorescent molecule, a quencher molecule, an amino group, or the like to the 3' position of the 3'-end nucleotide (via a linker, if necessary).

Specifically, in the polymorphism identification method of the present invention, first, the nucleic acid chain extension reaction is carried out by using; the nucleic acid in the test nucleic acid sample as a template, the type I detection primer, and a polymerase, with the existence of the inhibitory oligonucleotide (extension step).

The nucleic acid chain extension reaction may be performed either once or a plurality of times. For example, like a PCR method, a cycle consisting of the denaturation step, the annealing step, and the extension step can be repeated twice or more times. Even if the nucleic acid chain extension reaction is performed once only, the signal for detecting the yielded nucleic acid chain extension product can be enhanced by using nucleotides labeled with a fluorophore or the like.

In addition, the nucleic acid chain extension reaction may be either a reaction like PCR which requires a polymorphism-specific primer such as the type I detection primer and a polymorphism-nonspecific primer, or a reaction like an SSPCE (Sequence-Specific Primer Cycle Elongation) method (for example, refer to Current Pharmaceutical Biotechnology, 2003, Vol. 4, pp. 477-484) which uses only the type I detection primer.

The reaction condition of the nucleic acid chain extension reaction is not specifically limited and can be appropriately determined with consideration of: the type of the polymerase for use, the Tm values of the type I detection primer and the inhibitory oligonucleotide, and the like.

In addition, the reagents such as a polymerase, nucleotides, and a buffer for use in the nucleic acid chain extension reaction are not specifically limited, and those for use in usual nucleic acid chain extension reactions can be used at usual amounts.

The nucleic acid chain extension reaction of the present invention may be performed, like multiplex PCR, additionally with the presence of a detection primer which can hybridize with a region including the polymorphic site of a nucleic acid whose polymorphic site nucleotide sequence consists of a nucleotide sequence differing from that of the first nucleotide sequence. This detection primer other than the type I detection primer is preferably the type II detection primer which can hybridize with a region including the polymorphic site of the type II nucleic acid. In addition, when the polymorphism has three types of polymorphic site nucleotide sequences, the detection primer may be a primer which can hybridize with a nucleic acid whose polymorphic site nucleotide sequence consists of a nucleotide sequence differing from the first nucleotide sequence and the second nucleotide sequence.

The type II detection primer, similarly to the type I detection primer, may be any kind of primer which can hybridize with a partial region of the type II nucleic acid which contains the polymorphic site. The type II detection primer may be an oligonucleotide which comprises a nucleotide sequence completely complementary to the nucleotide sequence of the type II nucleic acid, or an oligonucleotide which comprises a nucleotide sequence complementary thereto except for one or several nucleotide mismatch(es). In addition, the type II detection primer may also have on its 5' side an additional nucleotide sequence besides the region which can hybridize with the type II nucleic acid. Moreover, the type II detection primer may be labeled. Examples of the additional nucleotide sequence and the labeling substance are similar to those of the type I detection primer.

Usually, the type I detection primer and the type II detection primer have common nucleotide sequences in the majority of their regions except for the polymorphism identification site. For this reason, the inhibitory oligonucleotide hybridizes not only with the type I detection primer but also with the type II detection primer. That is, the inhibitory oligonucleotide can also inhibit the nonspecific-nucleic acid chain extension reaction starting from the type II detection primer.

The type I detection primer, the type II detection primer, and the inhibitory oligonucleotide for use in the present invention can be designed by any method well known in the art, according to the nucleotide sequence of the identification target polymorphic site and the vicinity thereof. For example, these can be easily designed by using publicly known genome sequence data or SNP data with a general primer design tool. The publicly known genome sequence data is usually available on international nucleotide sequence databases, namely NCBI (National Center for Biotechnology Information), DDBJ (DNA Data Bank of Japan), and the like. Examples of the primer design tool include Primer3 (Rozen, S., H. J. Skaletsky, 1996, and Visual OMP (DNA Software) which are available on the web.

The thus designed primers and the like can be synthesized by any method well known in the art. For example, they may be synthesized by a custom oligo synthesis service or may be synthesized by a user him/herself using a commercially available synthesizer.

Next, the polymorphism of the nucleic acid contained in the test nucleic acid sample is identified depending on whether or not the type I detection primer has been extended in the extension step (identification step). That is, if a nucleic acid chain extension product starting from the type I detection primer is detected, the test nucleic acid sample can be determined to contain the type I nucleic acid.

For example, when the identification target polymorphism is a SNP having two types of polymorphism, namely a wild-type and a mutant, and when the nucleotide sequence of the mutant is regarded as the first nucleotide sequence and the nucleotide sequence of the wild-type is regarded as the second nucleotide sequence, then if a nucleic acid chain extension product of the type I detection primer is detected, the nucleic acid in the test nucleic acid sample can be determined to contain the mutant allele, and the donor of the test nucleic acid sample can be determined to have a homozygote or heterozygote of the mutant allele. On the other hand, when the identification target polymorphism is a somatic mutation, and when the nucleotide sequence of the mutant is regarded as the first nucleotide sequence and the nucleotide sequence of the normal type is regarded as the second nucleotide sequence, then if the nucleic acid chain extension product of the type I detection primer is detected, the nucleic acid in the test nucleic acid sample can be determined to contain the mutant nucleic acid, and the donor of the test nucleic acid sample can be determined to experience the somatic mutation.

The detection method of the nucleic acid chain extension product in the identification step is not specifically limited, and can be appropriately selected from known methods for use in quantitative measurements of nucleic acid chain extension products. For example, the detection may be done by electrophoresis or column chromatography based on the difference in the nucleotide length, or may be done by TOF-MS or such mass spectrometry.

When the detection primer is pre-labeled with a labeling substance, the detection can be done by the signal indication from the labeling substance. For example, when the detection primer is labeled with a fluorophore, the ratio of the amount of nucleic acid strand extension product to the amount of the unreacted primer can be measured by any one or more methods selected from the group consisting of Fluorescence Correlation Spectroscopy (hereinunder, referred to as FCS), Fluorescence Intensity Distribution Analysis (hereinunder, referred to as FIDA), and FIDA-polarization (hereinunder, referred to as FIDA-PO). Then, based on this ratio of the amount of nucleic acid strand extension product to the amount of the unreacted primer, the nucleic acid chain extension product can be detected.

Furthermore, if the type I detection primer and the inhibitory oligonucleotide used in the polymorphism identification method of the present invention are prepared as a kit set, the polymorphism identification method of the present invention can be more easily performed. In addition, the kit may also include an enzyme for use in the nucleic acid chain extension reaction, a buffer for preparing the reaction solution, nucleotides, and other reagents.

EXAMPLES

Next is a more detailed description of the present invention with reference to examples. However, the present invention is not to be considered as being limited by these examples.

Example 1

The polymorphism identification accuracy of the polymorphism identification method of the present invention was verified by performing SSP-PCR with or without the presence of the inhibitory oligonucleotide.

Specifically, the EGFR (epidermal growth factor receptor) gene mutation lacking amino acids at the position 746 to 750 (hereinunder, referred to as "EGFR_Exon_19_Del") which is a quite frequently found polymorphism in tumor cells, was identified using the polymorphism identification method of the present invention, and the identification accuracy thereof was investigated. FIG. 4 shows the alignments of the nucleotide sequences of the polymorphic site and its neighboring region of the wild-type (Wt) and the mutant (Mt) of the EGFR gene. The mutant lacked fifteen nucleotides.
Production of Detection Primer and Inhibitory Oligonucleotide Based on the nucleotide sequences shown in FIG. 4, the wild-type detection primer for detecting the wild-type nucleic acid, the mutant detection primer for detecting the mutant nucleic acid, and the inhibitory oligonucleotide were designed and produced. Table 1 shows the respective nucleotide sequences thereof. In the table, the symbol "Y" represents T (thymine) or C (cytosine).

Specifically, the mutant detection primer (2nd PCR Primer Mt: SEQ. ID. NO 1) was designed so that the seventh and eighth nucleotides from the 3' end can serve as the polymorphism detection site (the site where the seventh nucleotide from the 3' end can hybridize with the nucleotide corresponding to the first nucleotide of the codon at the amino acid position 750 of the wild-type gene, and the eighth nucleotide from the 3' end can hybridize with the nucleotide corresponding to the third nucleotide of the codon at the amino acid position 746 of the wild-type gene), and the nucleotides on the 5' side of the eighth nucleotide from the 3' end (the ninth and the following nucleotides) can serve as the common region (the region which can hybridize with the inhibitory oligonucleotide). The 5'-end nucleotide of the mutant detection primer was conjugated with the ATTO647N fluorophore (manufactured by ATTO-TEC GmbH) to label the primer with fluorescence (manufactured by SIGMA Genosys, HPLC grade).

Moreover, the wild-type detection primer (2nd PCR Primer Wt: SEQ. ID. NO 2) was designed so that the sixth to twenty second nucleotides from the 3' end can serve as the polymorphism detection site. The 5'-end nucleotide of the wild-type detection primer was conjugated with the TAMRA fluorophore (manufactured by SIGMA Genosys, HPLC grade).

Meanwhile, the inhibitory oligonucleotide was designed and produced so that it can hybridize with the common region of the mutant detection primer. Two types of inhibitory oligonucleotides were produced: "Inhibitor Oligo (−)" (SEQ. ID. NO 3) which was completely complementary to the common region of the mutant detection primer, and "Inhibitor Oligo (+)" which was complementary thereto except for one-nucleotide mismatch. In Table 1, the underlined nucleotide in the sequence of the "Inhibitor Oligo (+)" (SEQ. ID. NO 4) represents the mismatch site. The hydroxyl group of the 3'-end nucleotide thereof was modified with an amino group to hinder the function as a primer (manufactured by SIGMA Genosys, cartridge purification).

TABLE 1

| | Nucleotide sequence |
|---|---|
| 2nd PCR Primer Mt | (SEQ ID NO: 1)<br>ATTO- GTTGGCTTTCGGAGATGTYTTGATAG |
| 2nd PCR Primer Wt | (SEQ ID NO: 2)<br>TAMRA- CGGAGATGTTGCTTCTCTTAATTCC TTGATA |
| Inhibitor Oligo(−) | (SEQ ID NO: 3)<br>ACATCTCCGAAAGCCAAC-NH$_2$ |
| Inhibitor Oligo(+) | (SEQ ID NO: 4)<br>ACATCTCCG<u>T</u>AAGCCAAC-NH$_2$ |

Preparation of Standard Test Nucleic Acid Sample

In order to verify the identification accuracy for the EGFR_Exon_19_Del by using the polymorphism identification method of the present invention, the standard test nucleic acid samples containing the mutant nucleic acid and the wild-type nucleic acid at known content ratios were prepared.

First, the mutant nucleic acid and the wild-type nucleic acid were mixed so that the content ratio of the mutant nucleic acid (the ratio of the mutant nucleic acid relative to the total amount of the mutant nucleic acid and the wild-type nucleic acid) would be respectively 0%, 4%, 50%, and 100%, to thereby prepare a concentration series of the standard test nucleic acid sample with known content ratios of the mutant nucleic acid. The mutant nucleic acid and the wild-type nucleic acid used for the preparation of the standard test nucleic acid sample were obtained after PCR amplification using two types of primers shown in Table 2 (1st PCR-Primer 1 (SEQ. ID. NO. 5) and 1st PCR-Primer 2 (SEQ. ID. NO. 6), both manufactured by SIGMA Genosys, desalination grade) with the template nucleic acids respectively having the nucleotide sequences shown in FIG. 5 ("Wt 1st PCR product" (SEQ. ID. NO. 10) and "Mt 1st PCR product" (SEQ. ID. NO. 11)), and introduction into plasmids upon confirmation of the nucleotide sequences of the resultant amplification products.

TABLE 2

| | Nucleotide sequence |
|---|---|
| 1stPCR-Primer1 | (SEQ ID NO: 5)<br>AGGGAAAGACATAGAAAGTGAA |
| 1stPCR-Primer2 | (SEQ ID NO: 6)<br>TAATCAGTGTGATTCGTGGA |

In FIG. 5, the underlined regions on both ends of the "Wt 1st PCR product" and the "Mt 1st PCR product" represent regions of the respective PCR products which are derived from the two types of primers shown in Table 2. Moreover, the framed region in the "Wt 1st PCR product" represents the region to hybridize with the wild-type detection primer (2nd PCR Primer Wt). In addition, the framed region in the "Mt 1st PCR product" represents the region to hybridize with the mutant detection primer (2nd PCR Primer Mt), and the wave-lined region represents the region where the inhibitory oligonucleotide (Inhibitor Oligo) can hybridize with the mutant detection primer.

First Round PCR

In usual genetic tests, genomic fragments including the polymorphic site are pre-amplified so as to obtain a sufficient amount of template, and the thus obtained amplification product is used as a template to perform the nucleic acid chain extension reaction such as SSP-PCR for polymorphism identification.

Similarly, in this example, in order to obtain sufficient amounts of templates, the mutant nucleic acid and the wild-type nucleic acid were amplified by PCR using the prepared standard test nucleic acid sample as a template with the 1st PCR-Primer 1 and the 1st PCR-Primer 2. Since the same primers were used, this amplification would not affect the content ratio of the mutant nucleic acid in each sample.

Specifically, 2 µL of the standard test nucleic acid sample (20 ng/µL) was respectively added to 10 µL of 2x AmpliTaq Gold Master Mix (manufactured by ABI). The 1st PCR-Primer 1 and the 1st PCR-Primer 2 were added thereto at each final concentration of 0.1 µM, respectively. The resultant product was adjusted with pure water at the final volume of 20 µL, which was used as the reaction solution. This reaction solution was subjected to PCR amplification under the reaction condition consisting of: a treatment at 95° C. for 10 minutes, then 40 cycles at 95° C. for 30 seconds, 52° C. for 30 seconds, and 72° C. for 30 seconds, and an additional treatment at 72° C. for 10 minutes. The resulting PCR-reacted solution was used as the test nucleic acid sample after the amplification (amplified test nucleic acid sample).

Second Round PCR (SSP-PCR)

The amplified test nucleic acid sample after the amplification through the first round PCR was used as a template, and subjected to SSP-PCR with or without the presence of the inhibitory oligonucleotide. The Stoffel Fragment (manufactured by Applied Biosystems) was used as a DNA polymerase.

Specifically, in the reaction with the presence of the inhibitory oligonucleotide, 1 µL of each amplified test nucleic acid sample was added to 2 µL of 10× Buffer (manufactured by Applied Biosystems). The mutant detection primer, the wild-type detection primer, and the inhibitory oligonucleotide were added thereto at each final concentration of 0.01 µM, respectively. The resultant product was further added with 1.6 µL of dNTP Blend (10 mM, manufactured by TaKaRa), 2 µL of 25 mM $MgCl_2$, and 0.8 µL of the Stoffel Fragment (manufactured by Applied Biosystems). The mixture was adjusted with pure water at the final volume of 20 which was used as the reaction solution. These reaction solutions were subjected to SSP-PCR under the reaction condition consisting of: a treatment at 95° C. for 2 minutes, then 40 cycles at 95° C. for 30 seconds, 62° C. for 30 seconds, and 72° C. for 30 seconds, and an additional treatment at 72° C. for 10 minutes.

On the other hand, regarding the reaction solution, a solution prepared by adding an equal amount of pure water instead of the inhibitory oligonucleotide was used as a reaction solution for the reaction without the presence of the inhibitory oligonucleotide. These reaction solutions were subjected to SSP-PCR under the reaction condition consisting of: a treatment at 95° C. for 2 minutes, then 40 cycles at 95° C. for 30 seconds, 62° C. for 30 seconds, and 72° C. for 30 seconds, and an additional treatment at 72° C. for 10 minutes.

Measurement of Primer Consumption Rate

The PCR products resulting from the second round PCR were diluted 10-fold with 10 mM Tris-HCl, and measured for the primer consumption rates (K2%) of the mutant detection primer and the wild-type detection primer after the second round PCR respectively by the Fluorescence Correlation Spectroscopy (hereinunder, referred to as FCS).

Here, the primer consumption rate is a value calculated by the following equation.

Primer consumption rate=[amount of nucleic acid strand extension product]/[initial primer amount]
=[amount of nucleic acid strand extension product]/([amount of nucleic acid strand extension product]+[amount of unreacted primer])

FCS measurement was carried out with the fluorescence correlation spectrometer MF-20 (manufactured by Olympus). The measurement was for 15 seconds three times per each sample, and the average value thereof was used as the measurement result. Of the components resulting from the measurement, a component exhibiting a short diffusion time was assumed to be the unreacted primer and a component exhibiting a long diffusion time was assumed to be the nucleic acid chain extension product, by which the ratio of them was obtained. Then, based on this ratio, the primer consumption rate (K2%) was calculated.

FIG. 6 is a graph showing the measured consumption rate (K2%) of the mutant detection primer with variations of the content ratio of the mutant nucleic acid. In the graph, the term "Pn %" means that the content ratio of the mutant nucleic acid in the standard test nucleic acid sample used as the template is n %. In addition, the term "Without inhibitory oligo" shows the result obtained by adding no inhibitory oligonucleotide, the term "With inhibitory oligo" shows the result obtained by adding the inhibitory oligonucleotide "Inhibitor Oligo (−)" which had no mismatch, and the team "With inhibitory oligo+ mismatch" shows the result obtained by adding the inhibitory oligonucleotide "Inhibitor Oligo (+)" which has one-nucleotide mismatch.

As a result, when only the wild-type nucleic acid was used as a template (P0%), a signal showing a large molecular weight was detected in the FCS measurement without the addition of the inhibitory oligonucleotide, and its consumption rate of the mutant detection primer was not lower than 10%, confirming the production of the nucleic acid chain extension reaction product. On the other hand, with the addition of the inhibitory oligonucleotide, the consumption rate of the mutant detection primer was very low irrespective of the presence of mismatch.

Meanwhile, the case with the addition of the inhibitory oligonucleotide was similar to the case without the addition of the inhibitory oligonucleotide, in that the consumption rate of the mutant detection primer increased as the content ratio of the mutant nucleic acid increased in the reaction solution, confirming the detectability for the mutant nucleic acid.

Moreover, a tendency in which a signal from the specific nucleic acid chain extension reaction decreased by the addition of the inhibitory oligonucleotide, was observed. When the mismatch-containing inhibitory oligonucleotide was used, the primer consumption rate was very high, showing that the reduction of the signal from the specific nucleic acid chain extension reaction can be alleviated by including a mismatch in the inhibitory oligonucleotide.

INDUSTRIAL APPLICABILITY

The polymorphism detection method of the present invention is capable of satisfactory detecting a somatic mutation or such a polymorphism which requires high detection sensitivity, and thus is useful particularly in the field of genetic tests including SNP identification as well as clinical tests including analyses on tumor-related somatic mutations.

BRIEF DESCRIPTION OF THE REFERENCE SYMBOLS

1: Type I detection primer, 2: Inhibitory oligonucleotide, 3: Type I nucleic acid, 3*t*: Polymorphic site, 4: Type II nucleic acid, 4*t*: Polymorphic site, 2*m*: Mismatch site Sequence Listing

What is claimed is:

1. A polymorphism identification method for identifying a polymorphism of a polymorphic site-containing nucleic acid, comprising:

(a) preparing a reaction mixture, the mixture comprising:
a test nucleic acid sample as a template, wherein the test nucleic acid sample comprises a first nucleic acid comprising the polymorphic site;
a type I detection primer, wherein the type I detection primer comprises a polymorphism detection site, the type I detection primer comprising:
a template-binding region, and
an additional nucleic acid sequence added to the 5' end of the template-binding region, wherein the nucleotide sequence of the template-binding region is completely complementary to the nucleotide sequence of the first nucleic acid and not completely complementary to the nucleotide sequence of a second nucleic acid, and wherein the additional nucleic acid sequence is complementary to the nucleotide sequence adjacent to the 3' end of the template binding region, wherein the polymorphism detection site of the type I detection primer is located within five nucleotides from the 3' end of the type I detection primer;
an inhibitory oligonucleotide being complementary to the additional nucleic acid sequence;

(b) forming a complex comprising the template, the type I detection primer and the inhibitory oligonucleotide, wherein the template hybridizes the template-binding region of the type I detection primer, and wherein the inhibitory oligonucleotide hybridizes the additional nucleic acid sequence of the type I detection primer wherein a hybrid between the type I detection primer and the type I nucleic acid has a higher stability than a hybrid between the inhibitory oligonucleotide and the type I detection primer;

(c) performing a nucleic acid chain extension reaction in the reaction mixture; and (d) identifying the polymorphism of the test nucleic acid sample, based on the amount of the product of the chain reaction extension reaction in step (c).

2. The polymorphism identification method according to claim 1, wherein the 3' end nucleotide of the inhibitory oligonucleotide is blocked so that the oligonucleotide has no function as a primer.

3. The polymorphism identification method according to claim 1, wherein the length of the template-binding region is five nucleotides or more.

4. The polymorphism identification method according to claim 1, wherein the length of the region of the type I detection primer to hybridize with the inhibitory oligonucleotide is ten nucleotides or more.

5. The polymorphism identification method according to claim 1, wherein the nucleic acid chain extension reaction comprises:
(i) denaturing the nucleic acid in the test nucleic acid sample into single strands;
(ii) annealing the single-stranded nucleic acid with the type I detection primer and the inhibitory oligonucleotide, forming a hybrid of the type I detection primer and the single-stranded nucleic acid, and a hybrid between the type I detection primer and the inhibitory oligonucleotide; and
(iii) extending the nucleic acid strand starting from the type I detection primer;
wherein a Tm value of the hybrid between the type I detection primer and the inhibitory oligonucleotide is higher than a temperature of (ii), and lower than a temperature of (iii).

6. The polymorphism identification method according to claim 5, wherein a cycle consisting of (i), (ii), and (iii) is repeated twice or more times in the nucleic acid chain extension reaction.

7. The polymorphism identification method according to claim 1, wherein the nucleic acid chain extension reaction is performed on the second nucleotide sequence in the presence of a type II detection primer which can hybridize with a region including the polymorphic site thereof.

8. The polymorphism identification method according to claim 1, wherein the polymorphism detection site of the type I detection primer is located within two nucleotides from the 3' end of the type I detection primer.

9. The polymorphism identification method according to claim 8, wherein the polymorphism detection site of the type I detection primer is located at the 3' end of the type I detection primer.

10. The polymorphism identification method according to claim 1, wherein the nucleic acid sequence of the region of the inhibitory nucleotide to hybridize with the type I detection primer comprises at least one nucleotide mismatch.

11. A method for performing a nucleic acid chain extension reaction, comprising:

(a) preparing a reaction mixture, the mixture comprising:

a test nucleic acid sample as a template, wherein the test nucleic acid sample comprises a first nucleic acid comprising the polymorphic site, or the first nucleic acid comprising the polymorphic site and a second nucleic acid comprising the polymorphic site;

a type I detection primer comprising:

a template-binding region, and an additional nucleic acid sequence added to the 5' end of the template-binding region, wherein the nucleotide sequence of the template-binding region is completely complementary to the nucleotide sequence of the first nucleic acid and not completely complementary to the nucleotide sequence of the second nucleic acid, and wherein the additional nucleic acid sequence is complementary to the nucleotide sequence adjacent to the 3' end of the template binding region;

an inhibitory oligonucleotide being complementary to the additional nucleic acid sequence;

(b) forming a complex comprising the template, the type I detection primer and the inhibitory oligonucleotide, wherein the template hybridizes the template-binding region of the type I detection primer, and wherein the inhibitory oligonucleotide hybridizes the additional nucleic acid sequence of the type I detection primer; and (c) performing the nucleic acid chain extension reaction in the reaction mixture by repeating step (b).

12. A polymorphism identification method for identifying a polymorphism of a polymorphic site-containing nucleic acid, comprising:

(a) preparing a reaction mixture, the mixture comprising:

a test nucleic acid sample as a template, wherein the test nucleic acid sample comprises a first nucleic acid comprising the polymorphic site and a second nucleic acid comprising the polymorphic site;

a type I detection primer, wherein the type I detection primer comprises a polymorphism detection site, the type I detection primer comprising:

a template-binding region, and an additional nucleic acid sequence added to the 5' end of the template-binding region, wherein the nucleotide sequence of the template-binding region is completely complementary to the nucleotide sequence of the first nucleic acid and not completely complementary to the nucleotide sequence of the second nucleic acid, and wherein the additional nucleic acid sequence is complementary to the nucleotide sequence adjacent to the 3' end of the template binding region, wherein the polymorphism detection site of the type I detection primer is located within five nucleotides from the 3' end of the type I detection primer;

an inhibitory oligonucleotide being complementary to the additional nucleic acid sequence;

(b) forming a complex comprising the template, the type I detection primer and the inhibitory oligonucleotide, wherein the template hybridizes the template-binding region of the type I detection primer, and wherein the inhibitory oligonucleotide hybridizes the additional nucleic acid sequence of the type I detection primer wherein a hybrid between the type I detection primer and the type I nucleic acid has a higher stability than a hybrid between the inhibitory oligonucleotide and the type I detection primer;

(c) performing a nucleic acid chain extension reaction in the reaction mixture; and (d) identifying the polymorphism of the test nucleic acid sample, based on the amount of the product of the chain reaction extension reaction in step (c).

* * * * *

```
                        SEQUENCE LISTING

<160> NUMBER OF SEQ ID NOS: 11

<210> SEQ ID NO 1
<211> LENGTH: 26
<212> TYPE: DNA
<213> ORGANISM: Artificial Sequence
<220> FEATURE:
<223> OTHER INFORMATION: Synthetic Oligonucleotide, 2nd PCR Primer Mt

<400> SEQUENCE: 1
gttggctttc ggagatgtyt tgatag                                          26

<210> SEQ ID NO 2
<211> LENGTH: 31
<212> TYPE: DNA
<213> ORGANISM: Artificial Sequence
<220> FEATURE:
<223> OTHER INFORMATION: Synthetic Oligonucleotide, 2nd PCR Primer Wt

<400> SEQUENCE: 2
cggagatgtt gcttctctta attccttgat a                                    31

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide, Inhibitor Olig(-)

<400> SEQUENCE: 3
acatctccga aagccaac                                                   18

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide, Inhibitor Olig(+)

<400> SEQUENCE: 4
acatctccgt aagccaac                                                   18
```

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide, 1stPCR-Primer1

<400> SEQUENCE: 5
agggaaagac atagaaagtg aa                                          22

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide, 1stPCR-Primer2

<400> SEQUENCE: 6
taatcagtgt gattcgtgga                                             20

<210> SEQ ID NO 7
<211> LENGTH: 84
<212> TYPE: DNA
<213> ORGANISM: Homo sapiens

<400> SEQUENCE: 7
atcgaggatt tccttgttgg ctttcggaga tgttgcttct cttaattcct tgatagcgac    60
gggaatttta actttctcac cttc                                          84

<210> SEQ ID NO 8
<211> LENGTH: 34
<212> TYPE: DNA
<213> ORGANISM: Homo sapiens

<400> SEQUENCE: 8
atcgaggatt tccttgttgg ctttcggaga tgtt                              34

<210> SEQ ID NO 9
<211> LENGTH: 35
<212> TYPE: DNA
<213> ORGANISM: Homo sapiens

<400> SEQUENCE: 9
ttgatagcga cgggaatttt aactttctca ccttc                             35

<210> SEQ ID NO 10
<211> LENGTH: 441
<212> TYPE: DNA
<213> ORGANISM: Artificial Sequence
<220> FEATURE:
<223> OTHER INFORMATION: Synthetic nucleic acid, amplified product of
    wild type epidermal growth factor receptor gene exon 19.

<400> SEQUENCE: 10
agggaaagac atagaaagtg aacatttagg atgtggagat gagcagggtc tagagcagag    60
cagctgccag acatgagaaa aggtgggcct gaggttcaga gccatggacc cccacacagc   120
aaagcagaaa ctcacatcga ggatttcctt gttggctttc ggagatgttg cttctcttaa   180
ttccttgata gcgacgggaa ttttaacttt ctcaccttct gggatccaga gtccctatga   240
cagagagaga aggaagacgt taactggcaa ttgtgagatg gtgccacatg ctgcccagtg   300
atctgggtgg atgttaccag cgatgcaccc cgaaggtgag ggacactggg gctgtggagc   360
cgcacctaag gctgatattg ctgggggctg tgacgccccc gcagccctgc agctgttggg   420

```
ctccacgaat cacactgatt a                                              441

<210> SEQ ID NO 11
<211> LENGTH: 426
<212> TYPE: DNA
<213> ORGANISM: Artificial Sequence
<220> FEATURE:
<223> OTHER INFORMATION: Synthetic nucleic acid, amplified product of
      mutant epidermal growth factor receptor gene exon 19 Del.

<400> SEQUENCE: 11
agggaaagac atagaaagtg aacatttagg atgtggagat gagcagggtc tagagcagag    60
cagctgccag acatgagaaa aggtgggcct gaggttcaga gccatggacc cccacacagc   120
aaagcagaaa ctcacatcga ggatttcctt gttggctttc ggagatgttt tgatagcgac   180
gggaatttta actttctcac cttctgggat ccagagtccc tatgacagag agagaaggaa   240
gacgttaact ggcaattgtg agatggtgcc acatgctgcc cagtgatctg ggtggatgtt   300
accagcgatg caccccgaag gtgagggaca ctggggctgt ggagccgcac ctaaggctga   360
tattgctggg ggctgtgacg cccccgcagc cctgcagctg ttgggctcca cgaatcacac   420
tgatta                                                              426
```